United States Patent
Castan Barberan et al.

(10) Patent No.: US 10,617,619 B2
(45) Date of Patent: Apr. 14, 2020

(54) HAIR CONDITIONER

(71) Applicant: KAO Corporation S.A., Barbera del Valles (ES)

(72) Inventors: Pilar Castan Barberan, Barbera del Valles (ES); Judit Rodriguez Costero, Barbera del Valles (ES)

(73) Assignee: KAO Corporation S.A., Barbera del Valles (ES)

( * ) Notice: Subject to any disclaimer, the term of this patent is extended or adjusted under 35 U.S.C. 154(b) by 177 days.

(21) Appl. No.: 14/901,369

(22) PCT Filed: Jun. 23, 2014

(86) PCT No.: PCT/EP2014/063119
§ 371 (c)(1),
(2) Date: Dec. 28, 2015

(87) PCT Pub. No.: WO2014/206920
PCT Pub. Date: Dec. 31, 2014

(65) Prior Publication Data
US 2016/0143827 A1    May 26, 2016

(30) Foreign Application Priority Data

Jun. 26, 2013  (EP) ..................................... 13382248

(51) Int. Cl.
| | |
|---|---|
| *A61Q 5/12* | (2006.01) |
| *A61K 8/41* | (2006.01) |
| *A61K 8/34* | (2006.01) |
| *A61K 8/42* | (2006.01) |
| *A61K 8/02* | (2006.01) |
| *A61K 8/365* | (2006.01) |

(52) U.S. Cl.
CPC ............ *A61K 8/416* (2013.01); *A61K 8/0216* (2013.01); *A61K 8/342* (2013.01); *A61K 8/365* (2013.01); *A61K 8/42* (2013.01); *A61Q 5/12* (2013.01); *A61K 2800/592* (2013.01)

(58) Field of Classification Search
None
See application file for complete search history.

(56) References Cited

U.S. PATENT DOCUMENTS

| | | | |
|---|---|---|---|
| 4,891,214 A |  | 1/1990 | Stevens et al. |
| 6,274,128 B1 | * | 8/2001 | Bergmann ............... A61K 8/19 424/400 |
| 7,670,998 B2 | * | 3/2010 | Ambrosen ............. A61K 8/342 510/119 |
| 9,028,805 B2 |  | 5/2015 | Hoffman et al. |
| 2004/0146478 A1 |  | 7/2004 | Queralt et al. |
| 2007/0292380 A1 | * | 12/2007 | Staudigel ............... A61K 8/342 424/70.13 |
| 2011/0165110 A1 |  | 7/2011 | Kinoshita et al. |
| 2013/0131188 A1 | * | 5/2013 | Beckedahl ............... A61K 8/33 514/772 |

FOREIGN PATENT DOCUMENTS

WO      9731617 A1    9/1997

OTHER PUBLICATIONS

Minguet, M., Behenamidopropyl Dimethylamine: unique behaviour in solution and in hair care formulations, International Journal of Cosmetic Science, 2010, pp. 246-257, 32.

* cited by examiner

*Primary Examiner* — Jyothsna A Venkat
(74) *Attorney, Agent, or Firm* — Timothy J. Monahan; Monahan & Company, LLC

(57) ABSTRACT

The present invention relates to a composition comprising one or more quaternary ester ammonium compounds (a), one or more amidoamine compounds (b), wherein the weight ratio between the one or more quaternary ester ammonium compounds (a) and the one or more amidoamine compounds (b) is within a range of 1:5 to 5:1, and one or more fatty alcohols (c). The present invention also relates to a composition that is solid at room temperature, to a hair conditioner composition and to a method to prepare the hair conditioner composition by dispersing the solid composition in water at moderate temperatures.

10 Claims, No Drawings

HAIR CONDITIONER

FIELD OF THE INVENTION

The present invention relates to a composition (hereafter also referred to as a cosmetic composition) comprising one or more quaternary ester ammonium compounds, one or more amidoamine compounds and one or more fatty alcohols. Also, the present invention relates to cosmetic compositions being solid at room temperature, and to a liquid hair conditioner composition that can be prepared from that solid cosmetic compositions, and a method to prepare a liquid hair conditioner composition by dispersing said solid cosmetic composition in water at moderate temperatures.

STATE OF THE ART

Human hair can become soiled from the contact with environment and from sebum secreted by the scalp. This soiling may cause the hair to have a dirty or greasy feel, and an unattractive appearance.

Shampooing cleans the hair by removing the excess of soil and sebum. However, shampooing can leave the hair in a wet, tangled and generally unmanageable state. Once the hair dries, it is often left in a dry, rough, lusterless or frizzy condition due to the removal of the hair's natural oils and other natural conditioning and moisturizing components. It can be also left with increased levels of static upon drying which can interfere with combing, brushing and styling of hair. Hair conditioning compositions are widely known and are typically applied to the hair immediately after shampooing and rinsing the hair to avoid the problems described above and provides conditioning effect to the hair. The conditioning composition is worked through the hair, and may be then used as a leave-on conditioner or it can be rinsed from the hair with water.

Traditionally, hair conditioning compositions have used cationic surfactants. Cationic surfactants are those in which the surfactant activity resides in the positively charged cation portion of the molecule. The cationic surfactants are therefore attracted to the negatively charged hair surface and deposited on the hair. Among cationic surfactants, quaternary ammonium compounds and alkyl amidoamine compounds are particularly suited to the treatment of human hair. Thus, many hair conditioning products are based on quaternary ammonium compounds and alkyl amidoamine compounds.

An important requirement for hair conditioning compositions is a good performance even for damaged hair. It has been found that certain a combination of certain quaternary ester ammonium compound and certain alkyl amidoamine, provides a good performance in terms of combing force and antistatic effect especially for damaged hair.

Another requirement for hair conditioner products is low energy consumption during the preparation of said compositions. This aspect relates to the fact that hair conditioner compositions found in the market are liquid preparations while some of the cationic surfactants used as ingredients of said preparations are solid at room temperature and not dispersible in water at room temperature; even when previously melted, in order the cationics are dispersed in water it is need water temperature at least of 50-60° C. This is the case for alkylamidoamines. In order to disperse them in water it is needed or using water a temperature around 80° C. or melt the amidoamine an disperse it in water heated at around 60° C. The need of a melting step together with the need of using hot water involves energy consumption.

A way to eliminate the need of a melting step and simplify the hair conditioner preparation process is having a solid cosmetic composition which comprises one or more quaternary compounds as ingredient while being easily dispersible in water at moderate temperatures or even room temperature.

It is known in the prior art that the combination of certain quaternary ester ammonium compounds and certain alkyl amidoamine compounds at certain ratios, in addition of providing an advantageous performance with regard to the conditioning effect onto damaged hair, can be formulated with one or more fatty alcohols, to obtain a solid compound that can be easily dispersed in water at room temperature, being said dispersion suitable to obtain a good performing liquid hair conditioner.

Indeed, the combination of quaternary ester ammonium compounds and amidoamine is well known in the prior art. EP0786250 describes an aqueous formulation for conditioning hair comprising an active substance mixture comprising quaternary ammonium compounds (0.01-30% wt) and alkyl amidoamine compounds (0.01-30% wt) in addition to standard components. The treatment of human hair with the disclosed compositions lead to a good wet and dry combing advantageous coupled with good hair maintenance and low tendency to static electricity.

US20040146478 describes the use of mixtures comprising quaternary ammonium compounds and fatty acid amidoamine compounds for cosmetic preparations, especially for hair conditioner preparations, preferably in an emulsion form. The problem addressed was to provide transparent cosmetic preparations, more especially for hair care and particularly for conditioning the hair, which would allow the storage- and temperature-stable incorporation both of silicone oils and of antidandruff agent.

EP2394632 describes a hair conditioner composition being a solid or paste form at ambient temperature, aimed to provide an easily-handled hair conditioning composition with a very low water content and a low energy method of producing the same. The composition disclosed comprises a component (a) including higher alcohol with 16 carbon atoms or more, higher fatty acid with 16 carbon atoms or more and/or their derivatives, a component (b) being a cationic surfactant and a component (c) including polyhydric alcohol and/or polyethylene glycol having a melting point of 70° C. or less.

To conclude, it is clear to the inventors that there is still a need for better compositions. Thus, it is an object of the present invention to provide a composition that provides very good performance, particularly in terms of combing force and/or antistatic effect, especially advantageous for damaged hair, wherein the composition comprises quaternary ester ammonium compounds and alkyl amidoamine compounds in certain ratios, together in combination with fatty alcohols. Another object of the present invention is to provide a composition that is solid at room temperature. Another object of the present invention is to provide a hair conditioner composition and a method to prepare a hair conditioner composition by dispersing the solid composition according to the invention in water at moderate temperatures, thus obtaining a liquid hair conditioner.

SUMMARY OF THE INVENTION

According to the first aspect, the present invention provides a composition, said composition comprising:
    one or more quaternary ester ammonium compounds (a),
    one or more amidoamine compounds (b), one or more fatty alcohols (c),
wherein the weight ratio between the one or more quaternary ester ammonium compounds (a) and the one or more amidoamine compounds (b) is within a range of 1:5 to 5:1.

The composition is generally a cosmetic composition or a composition used for the manufacture of a cosmetic composition.

According to the second aspect, the present invention provides a room temperature solid cosmetic composition, said composition comprising:
one or more quaternary ester ammonium compounds (a),
one or more amidoamine compounds (b),
one or more fatty alcohols (c),
wherein the weight ratio between the one or more quaternary ester ammonium compounds (a) and the one or more amidoamine compounds (b) is within a range of 1:5 to 5:1, and wherein the water content in the solid cosmetic composition is 10 wt.-% or less.

According to the third aspect, the present invention provides a hair conditioner composition comprising:
one or more quaternary ester ammonium compounds (a),
one or more amidoamine compounds (b),
one or more fatty alcohols (c),
wherein the weight ratio between the one or more quaternary ester ammonium compounds (a) and the one or more amidoamine compounds (b) is within a range of 1:5 to 5:1, and wherein the water content in the hair conditioner composition is more than 10 wt.-%.

According to the fourth aspect, the present invention provides a method to prepare a hair conditioner composition by dispersing the solid cosmetic composition according to the second aspect of the present invention in water at a temperature within a range of 15° C. to 40° C., preferably within a range of 18 to 35° C., more preferably within a range of 20 to 30° C., most preferably at room temperature.

According to the fifth aspect, the present invention provides a use of the hair conditioner composition according to the third aspect of the present invention or obtained according to the fourth aspect of the present invention for the conditioning treatment of hair.

DETAILED DESCRIPTION OF THE INVENTION

In the present invention, room temperature is understood as a temperature in the range of 20° C. to 25° C.

All percentages are weight percentages, unless otherwise indicated. Active weight is the weight of the active matter with respect to the total weight of the composition, wherein by active matter it is understood the set of specific components responsible for a certain action. In the scope of the present application (i.e. with reference to the composition) the active matter is the totality of ingredients, from which are derived all or part of its effectiveness, particularly components (a), (b), and (c).

The main object of the present invention is a composition comprising:
one or more quaternary ester ammonium compounds (a),
one or more amidoamine compounds (b),
one or more fatty alcohols (c),
wherein the weight ratio between the one or more quaternary ester ammonium compounds (a) and the one or more amidoamine compounds (b) is within a range of 1:5 to 5:1.

In a preferred embodiment of the present invention, the one or more amidoamine compounds (b) is behenamidopropyl dimethylamine.

Quaternary Ester Ammonium Compound (a)

The present invention comprises one or more quaternary ester ammonium compounds (a), commonly known as esterquat, wherein the one or more quaternary ester ammonium compounds (a) preferably comprise at least a compound of formula (I) or even more preferably the one or more quaternary ester ammonium compounds (a) are all represented by formula (I):

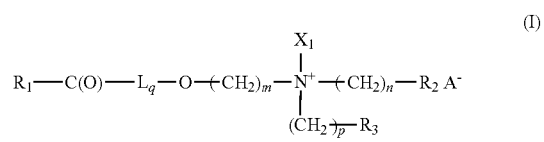

wherein
$X_1$ represents an hydroxyalkyl group containing 1 to 4 carbon atoms or an alkyl group containing 1 to 4 carbon atoms or an alkyl group containing one aromatic group, preferably $X_1$ is an alkyl group containing 1 to 4 carbon atoms, more preferably $X_1$ is a methyl group;

$R_1$ is a linear or branched alkyl or alkenyl group containing from 5 to 23 carbon atoms and from 0 to 3 double bonds, $R_2$ and $R_3$ each independently represent H, OH or —O-$L_q$-C(O)—$R_1$, L represents a —$(OCH_2CH_2)_a$—$(OR_4CHCH_2)_b$— group, wherein $R_4$ represents an alkyl group containing 1-4 carbon atoms, a represents an average number within the range of 0 to 20, b represents an average number within the range of 0 to 6, and the sum of a+b represents an average number within the range of 0 to 26, preferably from 0 to 10, more preferably from 0 to 6, most preferred 0, q represents an average number within the range of 0 to 26, m, n, and p each independently represent an average number within the range of 1 to 4, and A represents an anion.

In a preferred embodiment of the invention the quaternary ammonium compound of the invention are preferably non-ethoxylated, non-propoxylated.

In a preferred embodiment m, n, and p are equal to 2. In another preferred embodiment m and p are equal to 2 and n is equal to 1.

Also in a preferred embodiment, q represents an average number within the range of 0 to 10, more preferably within the range of 0 to 6, most preferred 0.

A preferably represents an halide, phosphate or alkylsulphate, more preferably an alkylsulphate, most preferred methylsulphate.

In preferred embodiments where q is not 0, and a+b is not 0, the quaternary ester ammonium compound of the invention is an ethoxylated and/or propoxylated esterquat. The order of sequence of the ethylene oxide and propylene oxide groups is not critical for the invention.

In one embodiment of the present invention, the one or more quaternary ester ammonium compounds (a) of formula (I) comprises a mixture of at least one or more mono-quaternary ester ammonium compounds, di-quaternary ester ammonium compounds or tri-quaternary ester ammonium compounds of formula (I.1), (I.2) and (I.3).

$$R_1-C(O)-L_q-O-(CH_2)_m-\underset{\underset{(CH_2)_p-R_3}{|}}{\overset{\overset{X_1}{|}}{N^+}}-(CH_2)_n-R_2 \ A^- \quad \text{I.1}$$

$$R_1-C(O)-L_q-O-(CH_2)_m-\underset{\underset{(CH_2)_p-O-L_q-C(O)-R_1}{|}}{\overset{\overset{X_1}{|}}{N^+}}-(CH_2)_n-R_2 \ A^- \quad \text{I.2}$$

$$R_1-C(O)-L_q-O-(CH_2)_m-\underset{\underset{(CH_2)_p-O-L_q-C(O)-R_1}{|}}{\overset{\overset{X_1}{|}}{N^+}}-(CH_2)_n-O-L_q-C(O)-R_1 \ A^- \quad \text{I.3}$$

wherein in formula I.1, I.2 and I.3

$R_2$ and $R_3$ each independently represent —H, or —OH, $X_1$ represents an hydroxyalkyl group containing 1 to 4 carbon atoms or an alkyl group containing 1 to 4 carbon atoms or an alkyl group containing one aromatic group, preferably $X_1$ is an alkyl group containing 1 to 4 carbon atoms, more preferably $X_1$ is a methyl group;

$R_1$ is a linear or branched alkyl or alkenyl group containing from 5 to 23 carbon atoms and from 0 to 3 double bonds, L represents a —(OCH$_2$CH$_2$)$_a$—(OR$_4$CHCH$_2$)$_b$— group, wherein $R_4$ represents an alkyl group containing 1-4 carbon atoms, a represents an average number within the range of 0 to 20, b represents an average number within the range of 0 to 6, and the sum of a+b represents an average number within the range of 0 to 26, preferably from 0 to 10, more preferably from 0 to 6, most preferred 0, q represents an average number within the range of 0 to 26, m, n, and p each independently represent an average number within the range of 1 to 4, and A represents an anion.

In another embodiment of the present invention, the one or more quaternary ester ammonium compounds (a) are obtained from triethanolamine or methyldiethanolamine or mixtures thereof, preferably from triethanolamine.

In particularly preferred methods of the invention, the compound of formula (I) is prepared by reacting triethanolamine or methyldiethanoalime or mixtures thereof, preferably triethanolamine, with a compound of formula R$^1$COOH or a derivative thereof (e.g. a chloride, anhydride or ester thereof) wherein R' is as hereinbefore defined.

Preferably the compound of formula R$^1$COOH is a C8-24 fatty acid. The fatty acid may be a natural product obtained from the oils and fats of plants and animals, such as palm, sunflower, soybean, olive, canola, tallow and tall oil. Alternatively a synthetic fatty acid may be used. Optionally the fatty acid is totally or partially hydrogenated. Optionally the fatty acid is purified. Preferably the fatty acid used has a purity of at least 90% by weight, more preferably at least 95% by weight, still more preferably at least 99% by weight. Since most natural sources of fatty acids comprise a mixture of different acids, natural products are preferably purified prior to use.

In one embodiment of the present invention, $R_1$ is a linear or branched alkyl or alkenyl group containing from 5 to 23 carbon atoms, preferably containing from 9 to 21 carbon atoms, more preferably containing from 14 to 21 carbon atoms; and 0 to 3 double bonds, preferably 0 or 1 double bonds.

Examples of linear or branched alkyl or alkenyl groups are products obtained from oils and fats from plants and animals, such as palm, coconut, sunflower, soybean, palm olein, olive, canola, tall oil or tallow, possibly totally or partially hydrogenated and purified, or synthetic fatty acids such as palmitoleic acid, oleic acid, elaidinic acid, petroselinic acid, linoleic acid, linolenic acid, gadoleic acid, behenic acid and erucic acid or mixtures thereof. Preferably palm and partially hydrogenated palm fatty acid are used.

Representative examples of C$_{8-24}$ fatty acids that may be used in the methods of the invention include palmitoleic acid, oleic acid, elaidinic acid, petroselinic acid, linoleic acid, linolenic acid, gadoleic acid, behenic acid and erucic acid, or mixtures thereof.

The reaction between the alkanolamine or akanolamine mixture and the compound of formula R$^1$COOH, e.g. C$_{8-24}$ fatty acid, is an esterification and it may be conducted under conditions known in the art, e.g. as described in patent application ES-A-2021900. The compounds of the invention are, however, diesters thus preferably the esterification reaction is carried out under conditions that maximizes the yield of diester.

The ratio of compound of formula R$^1$COOH or a derivative thereof, e.g. C$_{8-24}$ fatty acid, to the alkanolamine, e.g. triethanolamine, used in the esterification reaction is preferably lower than 2.5, more preferably between 1.2 and 2.5. Preferably the esterification reaction is carried out in the presence of a catalyst such as hypophosphorous acid or paratoluenesulfonic acid. Conventional stabilizers and/or antioxidants such as tocopherols, BHT, BHA, citric acid, etc may also be present in the esterification reaction mixture.

Preferably the esterification reaction is carried out at a temperature between 120° C. and 220° C. The preferred reaction time is 2-10 hours. Preferably the reaction is carried out a reduced pressure of about 5 to 200 mbar. The progress of the reaction may be monitored using conventional techniques, e.g. TLC or HPLC. The reaction may, for example, be monitored for consumption of compound of formula R$^1$COOH.

The product may also contain some unreacted compound of formula R$^1$COOH.

The composition is also likely to comprise methylated alkanolamine, methylated triethanolamine when ethanolamine is used.

Amidoamine Compounds (b)

The present invention comprises one or more amidoamine compounds (b), wherein the one or more amidoamine compounds (b) preferably comprise at least an amidoamine compound of formula (II) or even more preferably the one or more amidoamine compounds (b) are all represented by formula (II):

$$R_1-CO-NH-R_2-N\begin{matrix}R_3\\ \diagdown \\ R_4\end{matrix} \quad \text{(II)}$$

wherein
R₁ represents a linear or branched, saturated or unsaturated alkyl chain group containing from 8 to 36 carbon atoms,
R₂ represents a linear or branched alkylene group containing from 1 to 6 carbon atoms, and
R₃ and R₄ each independently represent a linear or branched alkyl group containing 1 to 3 carbon atoms.

In one embodiment of the present invention, the one or more amidoamine compounds (b) are represented by formula (II), wherein R₁ preferably represents a linear or branched, saturated or unsaturated alkyl chain group having from 6 to 24 carbon atoms, more preferably from 12 to 24 carbon atoms; R₂ represents a linear or branched alkylene group containing preferably 3 carbon atoms, and R₃ and R₄ each independently represent preferably a methyl group.

In another embodiment of the present invention, the amidoamine compounds (b) is selected from the group consisting of lauramidopropyl dimethylamine, myristamidopropyl dimethylamine, palmitamidopropyl dimethylamine, behenamidopropyl dimethylamine, stearamidopropyl dimethylamine, oleamidopropyl dimethylamine, and mixtures thereof.

In a specially preferred embodiment of the invention the amidoamine compounds (b) is behenamidopropyldimethylamine.

The one or more amidoamine compounds (b) are generally obtained by the reaction of a fatty acid (natural origin or technical mixture of fatty acids) and dimethylaminopropylamine.

Behenamidopropyldimethylamine can be obtained from the reaction of a behenic acid (docosanoic acid) composition and dimethylamino propyl amine.

Behenic acid dimethylaminopropylamide conforms to formula (II')

R—CO—NH(CH₂)₃—N(CH₃)₂     (II')

wherein R corresponds essentially to a $C_{21}$ alkyl group.

Behenic acid is preferably derived from natural fat and oil as well as synthetic triglycerides. Due to its possible natural origin, the fatty acid composition of behenic acid (i.e. the behenic acid composition) includes not only behenic acid, but also other fatty acids, such as small amounts of Palmitic Acid ($C_{16}$), Stearic Acid ($C_{18}$), Arachidic Acid ($C_{20}$), Lignoceric Acid ($C_{24}$) and others. Therefore, the content of behenic acid dimethylaminopropylamide, or a salt thereof, in the component b) is 60 wt. % or higher, preferably equal or higher than 75 wt. %. It is particularly preferred that the content of $C_{21}$ in R is equal or higher than 85 wt. % and the content of $C_{17}$ is lower than 5 wt. %

According to the invention, the salts of the behenic acid dimethylaminopropylamide are also possible use as compound b). Said salts are obtained by neutralizing or partially neutralizing the behenic acid dimethylaminopropylamide with organic and/or inorganic acids, like hydrochloric acid, phosphoric acid, acetic acid, lactic acid, glycolic acid, malic acid, succinic acid, citric acid, L-glutamic acid, pyroglutamic acid, $C_6$-$C_{22}$ fatty acids, like lauric acid, oleic acid, stearic acid and mixtures thereof, and alkyl ether carboxylic acids of formula

R—O—(CH₂CH₂O)ₙ—CH₂COOH wherein R represents a $C_2$-$C_{10}$ alkyl chain, preferably $C_6$-$C_8$ alkyl, and n has a value in the range of 1 to 10, preferably 3-8.

Examples of commercially available amidoamines are those corresponding to the commercial reference AMIDET® APA-18, (INCI Stearamidopropyl Dimethylamine), and AMIDET® APA-22 (INCI Behenamidopropyl Dimethylamine), all of them marketed by KAO Chemicals Europe.

Fatty Alcohols (c)

The present invention comprises one or more fatty alcohols (c), preferably the fatty alcohols (c) comprise fatty alcohols containing from 6 to 22 carbon atoms.

The C6-C22 fatty alcohols are aliphatic alcohols derived from natural fats and oils, as well as synthetic origin. Preferred fats and oils include palm oil, coconut oil, sunflower oil, rapeseed oil, castor oil, olive oil, soybean oil; and animal fat such as tallow, bone oil; fish oil, hardened oils and semi hardened oils thereof; and mixtures thereof.

Optionally, the C6-C22 fatty alcohols are ethoxylated and/or propoxylated, having an average alkoxylation degree from 1 to 30, preferably from 1 to 20, more preferably from 1 to 10, most preferred from 2 to 8.

In a preferred embodiment the fatty alcohols are not alkoxylated fatty alcohols.

Examples of C6-C22 fatty alcohols include capryl alcohol (1-octanol), pelargonic alcohol (1-nonanol), capric alcohol (1-decanol), lauryl alcohol (1-dodecanol), myristyl alcohol (1-tetradecanol), cetyl alcohol (1-hexadecanol), palmitoleyl alcohol (cis-9-hexadecan-1-ol), stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z,12Z-octadecadien-1-ol), elaidolinoleyl alcohol (9E,12E-octadecadien-1-ol), linolenyl alcohol (9Z,12Z,15Z-octadecatrien-1-ol), elaidolinolenyl alcohol (9E,12E,15-E-octadecatrien-1-ol), ricinoleyl alcohol (12-hydroxy-9-octadecen-1-ol), arachidyl alcohol (1-eicosanol), behenyl alcohol (1-docosanol), erucyl alcohol (cis-13-docosen-1-ol, and mixtures thereof.

Examples of commercially available fatty alcohols are those corresponding to the commercial reference KALCOL® 6098, (INCI Cetyl Alcohol, KALCOL® 8098 (INCI Stearyl Alcohol), KALCOL® 6850P, (INCI Cetearyl Alcohol), all of them marketed by KAO Chemicals Europe.

Cosmetic Composition of the Invention

The main object of the present invention is a cosmetic composition, comprising:
  one or more quaternary ester ammonium compounds (a),
  one or more amidoamine compounds (b),
  one or more fatty alcohols (c),
wherein the weight ratio between the one or more quaternary ester ammonium compounds (a) and the one or more amidoamine compounds (b) is within a range of 1:5 to 5:1.

In a preferred embodiment of the present invention, the weight ratio between the one or more quaternary ester ammonium compounds (a) and the one or more amidoamine compounds (b) is 1:3 and 3:1, more preferably 2:1.

In a specially preferred embodiment of the present invention, the cosmetic composition comprises one or more quaternary ester ammonium compounds (a), behenamidopropyl dimethylamine (b), and one or more fatty alcohols (c), wherein the weight ratio between the one or more quaternary ester ammonium compounds (a) and the behenamidopropyl dimethylamine (b) is within a range of 1:5 to 5:1.

In another preferred embodiment of the present invention, the cosmetic composition according to the invention is a room temperature solid cosmetic composition, wherein the water content in the solid cosmetic composition is 10 wt.-% or less.

In a further preferred embodiment, the cosmetic composition according to the invention is a room temperature solid cosmetic composition, wherein the water content in the solid cosmetic composition is 5 wt.-% or less, more preferably 3 wt.-% or less, most preferred 0.2 wt.-% wt or less.

In another embodiment of the present invention, the cosmetic composition comprises, 2.5% to 42%, preferably 13% to 25%, more preferably 20% to 24%, of the one or more quaternary ester ammonium compounds (a), 2.5% to 42%, preferably 6% to 25%, more preferably 7% to 15%, of the one or more amidoamine compounds (b), 50% to 83%, preferably 60% to 75%, more preferably 65% to 70%, of the one or more fatty alcohols (c), wherein the amounts indicated are expressed as percentage by active weight (with respect to the total weight of the composition).

The cosmetic composition of the present invention can be prepared by mixing one or more quaternary ester ammonium compounds (a), one or more amidoamine compounds (b) and one or more fatty alcohols (c) at 80° C. or 85° C. with stirring until complete homogenization, and then the mixture is cooled down to room temperature, whereby a solid suitable for pelleting can be obtained.

Hair Conditioner Composition:

The present invention further provides a hair conditioning composition comprising:
one or more quaternary ester ammonium compounds (a),
one or more amidoamine compounds (b),
one or more fatty alcohols (c),
wherein the weight ratio between the one or more quaternary ester ammonium compounds (a) and the one or more amidoamine compounds (b) is within a range of 1:5 to 5:1, and wherein the water content in the hair conditioner composition is more than 10 wt.-%, preferably more than 30 wt %, more preferably more than 50 wt %, even more preferably more than 80 wt, even more preferred more than 90 wt %, most preferred higher than 95 wt %.

In a preferred embodiment of the present invention, the weight ratio between the one or more quaternary ester ammonium compounds (a) and the one or more amidoamine compounds (b) is within a range of 1:3 and 3:1.

In another preferred embodiment of the present invention, the molar ratio between the one or more quaternary ester ammonium compounds (a) and the one or more amidoamine compounds (b) is within a range of 1:13 to 2:1, more preferably within the range of 1.26:1 to 1:8.

In a specially preferred embodiment of the present invention, the molar ratio between the one or more quaternary ester ammonium compounds (a) and the one or more amidoamine compounds (b) is 1:1.25.

Another aspect of the invention is a method to obtain the hair conditioner composition of the present invention, said method comprises a step a) of dispersing the solid composition according to the present invention in water, wherein the method is carried at a temperature within a range of 15 to 40° C., preferably within a range of to 35° C., more preferably within a range of 20 to 30° C., most preferably at room temperature.

The composition obtained by the above method is suitable for use as a hair conditioner. Thus, the use of the hair conditioner composition according to the invention or obtained according to the method as defined in the present invention for the conditioning treatment of hair is also part of the invention.

A method of conditioning human hair, wherein the hair conditioner composition according to the present invention or obtained according to the method as defined in the present invention is applied to the hair and further rinsed from the hair with water, or alternatively is left on hair as leave-on conditioner, is also a part of the invention The cosmetic composition and the hair conditioner composition according to the present invention may also comprise oil components, silicone compounds, powders, amphoteric surfactants, non-ionic surfactants, polymers, metal ion sequestering agents, UV protection factors, vitamins, antioxidants, antioxidant aids, perfume oils, germ inhibitors and the like as further auxiliaries and additives.

Examples of oils include liquid oils, solid oils, waxes, hydrocarbon oils and synthetic ester oils. Suitable oil components are, for example, Guerbet alcohols based on fatty alcohols containing 6 to 22 and preferably 8 to 10 carbon atoms, esters of linear C6-C22 fatty acids with linear C6-C22 fatty alcohols, esters of branched C6-C22 carboxylic acids with linear C6-C22 fatty alcohols such as, for example, myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isopropyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl cleats, erucyl behenate and erucyl erucate. Also suitable are esters of linear C6-C22 fatty acids with branched alcohols, more particularly 2-ethyl hexanol, esters of hydroxycarboxylic acids with linear or branched C6-C22 fatty alcohols, esters of linear and/or branched fatty acids with polyhydric alcohols for example propylene glycol, dimer diol or trimer triol) and/or Guerbet alcohols, triglycerides based on C6-C10 fatty acids, liquid mono-/di-/triglyceride mixtures based on C6-C18 fatty acids, esters of C6-C22 fatty alcohols and/or Guerbet alcohols with aromatic carboxylic acids, more particularly benzoic acid, esters of C6-C12 dicarboxylic acids with linear or branched alcohols containing 1 to 22 carbon atoms or polyols containing 2 to 10 carbon atoms and 2 to 6 hydroxyl groups, vegetable oils such as avocado oil, almond oil, hazelnut oil, babassu palm oil, borage oil, peanut oil, jojoba oil, canola oil, hemp oil, soybean oil, milk thistle oil, safflower oil, chufa oil, coconut oil, rapeseed oil, black cumin oil, wheat germ oil, sunflower oil, linseed oil, macadamia nut oil, corn oil, walnut oil, olive oil, branched primary alcohols, substituted cyclohexanes, linear and branched C6-C22 fatty alcohol carbonates, Guerbet carbonates, esters of benzoic acid with linear and/or branched C6-C22 alcohols, linear or branched, symmetrical or non-symmetrical dialkyl ethers containing 6 to 22 carbon atoms per alkyl group, ring opening products of epoxidized fatty acid esters with polyols, silicone oils and/or aliphatic or naphthenic hydrocarbons, for example dialkyl cyclohexanes.

Examples of waxes include natural waxes such as, for example, candelilla wax, carnauba wax, Japan wax, espartograss wax, cork wax, guaruma wax, rice oil wax, sugar cane wax, ouricury wax, montan wax, beeswax, shellac wax, spermaceti, lanolin (wool wax), uropygial fat, ceresine, ozocerite (earth wax), petrolatum, paraffin waxes, microwaxes; chemically modified waxes (hard waxes) such as for example, montan ester waxes, sasol waxes, hydrogenated jojoba waxes and synthetic waxes such as, for example, polyalkylene waxes and polyethylene glycol waxes Examples of hydrocarbon oils include liquid paraffin, squalane, pristane, paraffin, ceresin, squalene, petrolatum, and microcrystalline wax.

Suitable silicone compounds are, for example, dimethyl polysiloxanes, methylphenyl polysiloxanes, cyclic silicones and amino-, fatty acid-, alcohol-, polyether-, epoxy-, fluorine-, glycoside- and/or alkyl-modified silicone compounds which may be both liquid and resin-like at room temperature. Preferred silicone compounds are hydrophobic silicone oils, which are silicone oils which are soluble in paraffinic oil at 25° C. Hydrophobic silicone oils to be used according to the present invention include both volatile and non-volatile silicone oils.

Specific examples include a cyclic methyl siloxane having the formula $\{(CH3)2SiO\}_x$ in which x is 3-6, or short chain linear methyl siloxanes having the formula $((CH3)_2SiO\{(CH_3)_2SiO\}_y Si(CH_3)_3$ in which y is 0-5.

Some suitable cyclic methyl siloxanes are hexamethylcyclotrisiloxanes (D3), a solid with a boiling point of 134° C. and the formula $\{(Me_2)SiO\}_3$; octamethylcyclotetrasiloxane (D4) with a boiling point of 176° C., a viscosity of 2.3 mm²/s, and the formula $\{(Me_2)SiO\}_4$; decamethylcyclopentasiloxane (D5) (cyclomethicone) with a boiling point of 210° C., a viscosity of 3.87 mm²/s, and the formula $\{(Me_2)SiO\}_5$; and dodecamethylcyclohexasiloxane (DE) with a boiling point of 245° C., a viscosity of 6.62 mm²/s and the formula $\{(Me_2)SiO\}_6$.

Some suitable short linear methyl siloxane are hexamethyldisiloxane (MM) with a boiling point of 100° C., viscosity of 0-65 mm<2>/s, and formula $Me_3SiOMe_3$; octamethyltrisiloxane (MDM) with a boiling point of 152° C., viscosity of 1.04 mm²/s, and formula $Me_3SiOMe_2SiOSiMe_3$; decamethyltetrasiloxane (MD2M) with a boiling point of 194° C., viscosity of 1.53 mm²/s, and formula $Me_3SiO(MeSiO)_2SiMe_3$; dodecamethylpentasiloxane (MD3M) with a boiling point of 229° C., viscosity of 2.06 mm²/s, and formula $Me_3SiO(Me_2SiO)_3SiMe_3$; tetradecamethylhexasiloxane (MD4M) with a boiling point of 245° C., viscosity of 2.63 mm²/s, and formula $Me_3SiO(Me_2SiO)_4SiMe_3$; and hexadecamethylheptasiloxane (MD5M) with a boiling point of 270° C., viscosity of 3.24 mm²/s, and formula $Me_3SiO(Me_2SiO)_5SiMe_3$.

Furthermore, long chain linear siloxanes such as phenyltrimethicone, bis(phenylpropyl)dimethicone, dimethicone, and dimethiconol are also included.

Examples of powders include inorganic powders such as talc, kaolin, mica, sericite, muscovite, phlogopite, synthetic mica, lepidolite, biotite, vermiculite, bentonite, hectorite, laponite, magnesium carbonate, calcium carbonate, aluminum silicate, barium silicate, calcium silicate, magnesium silicate, strontium silicate, tungstate, magnesium, silica, zeolite, barium sulfate, calcined calcium sulfate (calcined gypsum), calcium phosphate, fluorine apatite, hydroxyapatite, ceramic powder, metallic soap (e.g., zinc myristate, calcium palimitate, and aluminum stearate), and boron nitride; organic powders such as polyamide resin powder (nylon powder), polyethylene powder, polymethylmethacrylate powder, polystyrene powder, styrene-acrylic acid copolymer resin powder, benzoguanamine resin powder, poly(tetrafluroethylene) powder, and cellulose powder; inorganic white pigments such as titanium dioxide and zinc oxide; inorganic red pigments such as iron oxide (red iron oxide) and iron titanate; inorganic brown pigments such as γ-iron oxide; inorganic yellow pigments such as yellow iron oxide and ocher; inorganic black pigments such as black iron oxide and lower order titanium oxide; inorganic purple pigments such as mango violet and cobalt violet; inorganic green pigments such as chrome oxide, chrome hydroxide, and cobalt titanate; inorganic blue pigments such as ultramarine and Prussian blue; pearl pigments such as titanium oxide coated mica, titanium oxide coated bismuth oxychloride, titanium oxide coated talc, colored titanium oxide coated mica, bismuth oxychloride, and fish scale flakes; metal powder pigments such as aluminum powder and copper powder; organic pigments such as zirconium, barium, or aluminum lake (e.g., organic pigments such as Red No. 201, Red No. 202, Red No. 204, Red No. 205, Red No. 220, Red No. 226, Red No. 228, Red No. 405, Orange No. 203, Orange No. 204, Yellow No. 205, Yellow No. 401, and Blue No. 404, or Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1); and natural colors such as chlorophyll and β-carotene.

Examples of amphoteric surfactants include imidazoline type amphoteric surfactants such as sodium 2-undecyl-N,N,N-(hydroxyethylcarboxymethyl)-2-imidazoline and 2-cocoyl-2-imidazolinium hydroxide-1-carboxyethyloxy)-2-sodium salt; betaine type surfactants such as 2-heptadecyl-N-carboxymethyl-N-hydroxyethylimidazolinium betaine, lauryldimethyl aminoacetate betaine, alkyl betaine, amidobetaine, and sulfobetaine.

Examples of lipophilic nonionic surfactants include sorbitan fatty acid esters (such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate); glycerol or polyglycerol fatty acid esters (such as glycerol mono-cotton seed oil fatty acid ester, glycerol monoerucate, glycerol sesquioleate, glycerol monostearate, glycerol-α,α'-oleate pyroglutamate, and glycerol monostearate malate); propylene glycol fatty acid esters (such as propylene glycol monostearate); hardened castor oil derivatives; and glycerol alkyl ethers.

Examples of hydrophilic nonionic surfactants include POE-sorbitan fatty acid esters (such as POE-sorbitan monooleate, POE-sorbitan monostearate, and POE-sorbitan tetraoleate); POE sorbitol fatty acid esters (such as POE-sorbitol monolaurate, POE-sorbitol monooleate, POE-sorbitol pentaoleate, and POE-sorbitol monostearate); POE-glycerol fatty acid esters (such as POE-monooleates, POE-glycerol monostearate, POE-glycerol monoisostearate, and POE-glycerol triisostearate); POE-fatty acid esters (such as POE-distearate, POE-monodioleate, and ethylene glycol distearate); POE-alkyl ethers (such as POE-lauryl ether, POE-oleyl ether, POE-stearyl ether, POE-behenyl ether, POE-2-octyldodecyl ether, and POE-cholestanol ether); Pluronic type surfactants (such as Pluronic); POE/POP-alkyl ethers (such as POE/POP cetyl ether, POE/POP 2-decyltetradecyl ether, POE/POP monobutyl ether, POE/POP hydrogenated lanolin, and POE/POP glycerol ether); tetra POE/tetra POP-ethylenediamine condensates (such as Tetronic); POE-castor oil or hardened castor oil derivatives (such as POE-castor oil, POE-hardened castor oil, POE-hardened castor oil monoisostearate, POE-hardened castor oil triisostearate, POE-hardened castor oil monopyroglutamate monoisostearate diester, and POE-hardened castor oil maleate); POE-beeswax lanolin derivatives (such as POE-sorbitol beeswax); alkanolamides (such as coconut oil fatty acid diethanolamide, lauric acid monoethanolamide, and fatty acid isopropanolamide); POE-propylene glycol fatty acid esters; POE-alkylamines; POE-fatty acid amides; sucrose fatty acid esters; alkylethoxydimethylamine oxides; and trioleyl phosphate.

Suitable cationic polymers are, for example, cationic cellulose derivatives such as, for example, the quaternized hydroxyethyl cellulose obtainable from Amerchol under the name of Polymer JR 400, cationic starch, copolymers of diallyl ammonium salts and acrylamides, quaternized vinyl pyrrolidone/vinyl imidazole polymers such as, for example, Luviquat (BASF), condensation products of polyglycols and amines, quaternized collagen polypeptides such as, for example, Lauryidimonium Hydroxypropyl Hydrolyzed Collagen, quaternized wheat polypeptides, polyethyleneimine, cationic silicone polymers such as, for example, Amodimethicone, copolymers of adipic acid and dimethylaminohydroxypropyl diethylenetriamine (Cartaretine, Sandoz), copolymers of acrylic acid with dimethyl diallyl ammonium chloride, polyquaternium type polymers, polyaminopolyamides and crosslinked water-soluble polymers thereof, cationic chitin derivatives such as, for example, quaternized chitosan, optionally in micro-crystalline distribution, condensation products of dihaloalkyls, for example dibromobutane, with bis-dialkylamines, for example bis-dimethylamino-1,3-propane, cationic guar gum such as, for example, Jaguar CBS, Jaguar C-17, Jaguar C-16 of Celanese, quaternized ammonium salt polymers such as, for example, Mirapol A-15, Mirapol AD-1, Mirapol AZ-1 of Mirapol.

Suitable anionic, zwitterionic, amphoteric and nonionic polymers are, for example, vinyl acetate/crotonic acid copolymers, vinyl pyrrolidone/vinyl acrylate copolymers, vinyl acetate/butyl maleate/isobornyl acrylate copolymers, methyl vinylether/maleic anhydride copolymers and esters thereof, uncrosslinked and polyol-crosslinked polyacrylic acids, acrylamidopropyl trimethylammonium chloride/acrylate copolymers, octylacrylamide/methyl methacrylate/tert.-butylaminoethyl methacrylate/2-hydroxypropyl methacrylate copolymers, polyvinyl pyrrolidone, vinyl pyrrolidone/vinyl, acetate copolymers, vinyl pyrrolidone/dimethylaminoethyl methacrylate/vinyl caprolactam terpolymers and optionally derivatized cellulose ethers and silicones.

Examples of UV protection factors include organic substances (light filters) which are liquid or crystalline at room temperature and which are capable of absorbing ultraviolet radiation and of releasing the energy absorbed in the form of longer-wave radiation, for example heat. UV-B filters can be oil-soluble or water-soluble. The following are examples of oil-soluble substances: 3-benzylidene camphor or 3-benzylidene norcamphor and derivatives thereof, for example 3-(4-methylbenzylidene)-camphor; 4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid Amylester; esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene); esters of salicylic acid, preferably salicylic acid-2-ethylhexyl ester, salicylic acid-4-isopropylbenzyl ester, salicylic acid homomethyl ester; derivatives of benzophenone, preferably 2-hydroxy-4-methoxybenzo-phenone, 2-hydroxy-4-methoxy-4'-methylbenzophenone, 2,2'-dihydroxy-4-methoxybenzophenone; esters of benzalmalonic acid, preferably 4-methoxybenzalmalonic acid di-2-ethylhexyl ester; triazine derivatives such as, for example, 2,4,6-trianilino-(p-carbo-2'-ethyl-1'-hexyloxy)-1,3,5-triazine and Octyl Triazone; propane-1,3-dionessuch as, for example, 1-(4-tert.butylphenyl)-3-(4T-methoxyphenyl)-propane-1,3-dione; 2-phenylbenzimidazole-5-sulfonic acid and alkali metal, alkaline earth metal, ammonium, alkylammonium, alkanolammonium and glucammonium salts thereof; sulfonic acid derivatives of benzophenones, preferably 2-hydroxy-4-methoxybenzophenone-5-sulfonic acid and salts thereof; sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example 1-(4'-tert.butylphenyl)-3-(4'-methoxyphenyl)-propane-1,3-dione, 4-tert-butyl-4'-methoxydibenzoyl methane (Parsol 1789) or 1-phenyl-3-(4'-isopropylphenyl)-propane-1,3-dione.

The UV-A and UV-B filters may of course also be used in the form of mixtures. Besides the soluble substances mentioned, insoluble pigments, i.e. finely dispersed metal oxides or salts, may also be used for this purpose. Examples of suitable metal oxides are, in particular, zinc oxide and titanium dioxide and also oxides of iron, zirconium, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have an average diameter of less than 100 nm, preferably from 5 to 50 nm and more preferably from 15 to 30 nm. They may be spherical in shape although ellipsoidal particles or other non-spherical particles may also be used. The pigments may also be surface-treated, i.e. hydrophilicized or hydrophobicized. Typical examples are coated titanium dioxides such as, for example, Titandioxid T 805 (Degussa) or Eusolex T2000 (Merck). Suitable hydrophobic coating materials are, above all, silicones and especially trialkoxyoctyl silanes or simethicones. So-called micro- or nanopigments are preferably used in sun protection products. Micronized zinc oxide is preferably used.

Besides the two above-mentioned groups of primary protection factors, secondary protection factors of the antioxidant type may also be used. Secondary sun protection factors of the antioxidant type interrupt the photochemical reaction chain which is initiated when UV rays penetrate into the skin. Typical examples of suitable antioxidants are amino acids (for example glycine, histidine, tyrosine, tryptophane) and derivatives thereof, imidazoles (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, liponic acid and derivatives thereof (for example dihydroliponic acid), aurothioglucose, propylthiouracil and other thiols (for example thioredoxine, glutathione, cysteine, cystine, cystamine and glycosyl, N-acetyl, methyl, ethyl, propyl, amyl, butyl and lauryl, palmitoyl, oleyl, γ-linoleyl, cholesteryl and glyceryl esters thereof) and their salts, dilaurylthiodipropionate, distearylthiodipropionate, thiodipropionic acid and derivatives thereof (esters, ethers, peptides, lipids, nucleotides, nucleosides and salts) and sulfoximine compounds (for example butionine sulfoximines, homocysteine sulfoximine, butionine sulfones, penta-, hexa- and hepta-thionine sulfoximine) in very small compatible dosages (also (metal) chelators (for example α-hydroxyfatty acids, palmitic acid, phytic acid, lactoferrine), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof (for example γ-linolenic acid, linoleic acid, oleic acid), folic acid and derivatives thereof, ubiquinone and ubiquinol and derivatives thereof, vitamin C and derivatives thereof (for example ascorbyl palmitate, Mg ascorbyl phosphate, ascorbyl acetate), tocopherols and derivatives (for example vitamin E acetate), vitamin A and derivatives (vitamin A palmitate) and coniferyl benzoate of benzoin resin, rutinic acid and derivatives thereof, (α-glycosyl rutin, ferulic acid, furfurylidene glucitol, carnosine, butyl hydroxytoluene, butyl hydroxyanisole, nordihydroguaiac resin acid, nordihydroguaiaretic acid, trihydroxy-butyrophenone, uric acid and derivatives thereof, mannose and derivatives thereof, Superoxid-Dismutase, zinc and derivatives thereof (for example ZnO, ZnSO4), selenium and derivatives thereof (for example selenium methionine), stilbenes and derivatives thereof (for example stilbene oxide, trans-stilbene oxide) and derivatives of these active substances suitable for the purposes of the invention (salts, esters, ethers, sugars, nucleotides, nucleosides, peptides and lipids).

Examples of metal ion sequestering agents include 1-hydroxyethane-1,1-diphosphonic acid, 1-hydroxyethane-1,1-diphosphonic acid 4Na salt, disodium edetate, trisodium edetate, tetrasorium edetate, sodium citrate, sodium polyphosphate, sodium metaphosphate, gluconic acid, phosphoric acid, citric acid, ascorbic acid, succinic acid, edetic acid, and trisodium hydroxyethyl ethylenediamine triacetate.

Examples of vitamins include vitamins A, B1, B2, B6, C, and E and the derivatives thereof; pantothenic acid and the derivatives thereof; and biotin.

Examples of antioxidants include tocopherols, dibutylhydroxytoluene, butylhydroxyanisole, and gallic acid esters. Examples of antioxidant aids include phosphoric acid, citric acid, ascorbic acid, maleic acid, malonic acid, succinic acid, lactic acid, fumaric acid, cephalin, hexametaphosphates, phytic acid, and ethylenediaminetetraacetic acid.

Suitable perfume oils are mixtures of natural and synthetic fragrances. Natural fragrances include the extracts of blossoms (lily, lavender, rose, jasmine, neroli, ylang-ylang), stems and leaves (geranium, patchouli, petitgrain), fruits (anise, coriander, caraway, juniper), fruit peel (bergamot, lemon, orange), roots (nutmeg, angelica, celery, cardamon, costus, iris, calmus), woods (pinewood, sandalwood, guaiac wood, cedarwood, rosewood), herbs and grasses (tarragon, lemon grass, sage, thyme), needles and branches (spruce, fir, pine, dwarf pine), resins and balsams (galbanum, elemi, benzoin, myrrh, olibanum, opoponax). Animal raw materials, for example civet and beaver, may also be used. Typical synthetic perfume compounds are products of the ester, ether, aldehyde, ketone, alcohol and hydrocarbon type. Examples of perfume compounds of the ester type are benzyl acetate, phenoxyethyl isobutyrate, p-tert-butyl cyclohexylacetate, linalyl acetate, dimethyl benzyl carbinyl acetate, phenyl ethyl acetate, linalyl benzoate, benzyl formate, ethylmethyl phenyl glycinate, allyl cyclohexyl propionate, styrallyl propionate and benzyl salicylate. Ethers include, for example, benzyl ethyl ether while aldehydes include, for example, the linear alkanals containing 8 to 18 carbon atoms, citral, citronellal, citronellyloxyacetaldehyde, cyclamen aldehyde, hydroxycitronellal, filial and bourgeonal. Examples of suitable ketones are the iononones, α-isomethylionone and methyl cedryl ketone. Suitable alcohols are anethol, citronellol, eugenol, isoeugenol, geraniol, linalool, phenylethyl alcohol and terpineol. The hydrocarbons mainly include the terpenes and balsams. However, it is preferred to use mixtures of different perfume compounds which, together, produce an agreeable fragrance. Other suitable perfume oils are essential oils of relatively low volatility which are mostly used as aroma components. Examples are sage oil, camomile oil, clove oil, melissa oil, mint oil, cinnamon leaf oil, lime-blossom oil, juniper berry oil, vetiver oil, olibanum oil, galbanum oil, labolanum oil and lavendin oil. The following are preferably used either individually or in the farm of mixtures: bergamot oil, dihydromyrcenol, lilial, lyral, citronellol, phenylethyl alcohol, α-nexylcinnamaldehyde, geraniol, benzyl acetone, cyclamen aldehyde, linalool, Boisambrene Forte, Ambroxan, indole, hedione, sandelice, citrus oil, mandarin oil, orange oil, allylamyl glycolate, cyclovertal, lavendin oil, clary oil, β-damascone, geranium oil bourbon, cyclohexyl salicylate, Vertofix Coeur, Iso-E-Super, Fixolide NP, evernyl, iraldein gamma, phenylacetic acid, geranyl acetate, benzyl acetate, rose oxide, romillat, irotyl and floramat.

Typical examples of germ inhibitors are preservatives which act specifically against gram-positive bacteria such as, for example, 2,4,4'-trichloro-2'-hydroxydiphenyl ether, chlorhexidine (1,6-di-(4-chlorophenyl-biguanido)-hexane) or TCC (3,4,4'-trichlorocarbanilide). Numerous perfumes and essential oils also have antimicrobial properties. Typical examples are the active substances eugenol, menthol and thymol in clove, mint and thyme oil.

The following examples are given in order to provide a person skilled in the art with a sufficiently clear and complete explanation of the present invention, but should not be considered as limiting of the essential aspects of its subject, as set out in the preceding portions of this description.

EXAMPLES

Preparation of Solid Composition According to the Invention

In the following a non-limiting example for the preparation of a solid composition according to the invention is provided (general method).

220 grams of palm fatty acid acid were introduced in an inert atmosphere into a stainless steel reactor, and 74.9 grams of triethanolamine were added with stirring. The mixture was heated for at least 4 hours at 160-180° C. in order to remove the water of the reaction. The progress of the reaction was monitored by an acid/base assay which determines the residual acidity to obtain an esterification of at least 90% of the fatty acids.

280.4 g of a yellowish liquid product, consisting essentially of a mixture of unesterified fatty acids, mono-, di- and triesterified triethanolamine and unreacted triethanolamine amine may also remain. For the quaternisation, 58.1 grams of dimethyl sulphate were added with stirring at a temperature of 50-90° C. to 271.4 grams of the product obtained from the esterification. After four hours of digestion, the virtually complete absence of residual amine was verified by acid/base assay. After obtain 329.5 grams of the esterquat (EQ-HC) were diluted with 989.1 grams of cetearyl alcohol. Keeping the product under inert and stirring conditions, 133.9 grams of behenamidopropyldimethylamine were added to have a complete homogenization. Once the product was homogeneous it was cooled down to room temperature. Some of the compositions were neutralized with lactic acid in order to form the amine salt of the amidoamine (cationic surfactant) and some of them were not neutralized.

Table 1 shows the ingredients used to prepared solid compositions. The amounts for each component indicated in Table 1 are indicated in percentage of active weight of each ingredient, and were prepared following the general method.

Table 2 summarizes the physical properties of the compositions prepared in defined in Table 1.

TABLE 1

| % | A | B | C | D | E | F | G | H | C1 |
|---|---|---|---|---|---|---|---|---|---|
| EQ HC[1] | 22.7 | 22.1 | 22.7 | 22.1 | 14.6 | 14.2 | 14.7 | 14.2 | — |
| Cetyl Alcohol | — | — | — | — | 36.7 | 35.7 | 36.8 | 35.7 | — |
| Stearyl Alcohol | — | — | — | — | 36.7 | 35.7 | 36.8 | 35.7 | — |
| Cetearyl Alcohol (50:50) | 68.0 | 66.5 | 68.2 | 66.5 | — | — | — | — | 66.6 |
| Behenamidopropyldimethylamine | 9.21 | 9.00 | — | — | 11.8 | 11.5 | — | — | — |
| Stereamidopropyldimethylamine | — | — | 8.98 | 8.75 | — | — | 11.6 | 11.2 | 13.4 |
| Lactic Acid 90% | — | 2.31 | — | 2.57 | — | 2.71 | — | 3.03 | 3.22 |
| Behentrimonium Chloride | — | — | — | — | — | — | — | — | 16.7 |
| Ratio (a):(b) | 2.46:1 | 1.96:1 | 2.53:1 | 1.96:1 | 1.23:1 | 1:1 | 1.27:1 | 1:1 | 1.25:1(*) |

(*)In this case the ratio a:b does not apply, the FIG. 1.25:1 refers to the weight ratio between the quaternary ammonium compound and the amidoamine.

TABLE 2

| | A | B | C | D | E | F | G | H |
|---|---|---|---|---|---|---|---|---|
| Hygroscopicity (20° C., 80% HR, 48 h) | ◯ | Δ | ◯ | Δ | ◯ | Δ | ◯ | Δ |
| Penetrability (1/10 mm, 150 g, 30 sec) | ⊙ | ⊙ | ⊙ | ⊙ | ⊙ | Δ | ⊙ | Δ |
| Rheology | ⊙ | ◯ | ⊙ | ◯ | ⊙ | ◯ | ⊙ | ◯ |

⊙, ◯, Δ, X: Excellent, good, fair, bad

All products in Table 2 are light colored solids, and their melting point (Differential Scanning calorimeter DSC-Q20 (TA Instruments)) is between 60 and 70° C.

Hygroscopicity was measured by storing the sample at 20° C. and 80% relative humidity and weighting the sample after specific times under these conditions.

Hardness was indirectly measured by penetrability by using a penetrometer (Normatest). The higher the penetrability the lower the hardness of the sample is.

Samples with penetrability below 30 and melting points above 43° C. are considered able to make pellets.

Samples were melted and let cool down to room temperature for 24 hours before measuring penetrability. The applied weight for the measurements was 150 g during 30 seconds and the penetrability of the needle was read in the penetrometer.

Rheograms of viscosity vs. temperature were measured by using a Haake Rhestress 600 rheometer (Thermo-Fischer) in order to find out the fluidity of each composition. Conditions: 85 to 30° C., ω=20l/s, #13.

For all the properties, the compositions comprising Behenamidopropyl Dimethylamine, i.e. samples A, B, E and F, are preferred. Not neutralized samples (A and E) are even more preferred.

Dispersing Ability at Room Temperature

All the samples described Table 1 are light colored solids, but only samples A, B, E and F of Table 1, containing the esterquat, Behenamidopropyl Dimethylamine and fatty alcohol are able to disperse at room temperature in water only by mechanical stirring, and without the need of heating.

The dispersing ability in water at room temperature was evaluated after preparing 300 grams of sample by stirring the compositions described above (1.5% active cationic (esterquat and amidoamine) and 3% fatty alcohol) in water for 2 hours at 25° C. at 250 rpm. Then samples were filtered by an ASTM 50 filter (300 micron) under pressure. The residue left on the filter was then dried for 24 hours at 50° C. and weighted. Only compositions A, B, E and F were possible to filter completely. Thus, these composition are preferred having regard to the present invention.

In the rest of the samples, a big solid residue made impossible to complete the filtration of the sample. This indicates that these products could not be completely dispersed at room temperature.

Performance in Hair Conditioner Composition

Performance was also evaluated in formulations shown in Table 3. Combing force of hair conditioners prepared containing esterquat and amidoamines at two different ratios (all ratios are in active matter). All formulations contain 1.5% active cationic (quaternary ester ammonium compound and amidoamine) and 3% fatty alcohol.

Combing force reduction is one of the advantageous characteristics of the composition, as it is a measure of a good performance.

Combing forces were determined using a dynamometer (Instron 5543, cell 1 kg, rate 500 mm/min). A Caucasian damaged hair tress of approximately 20 g and 22 cm in length was combed 10 times under wet and dry conditions and the values obtained were averaged.

As can be seen, the compositions according to the invention have very low combing forces.

TABLE 3

| | Weight Ratio | Combing force (gf) |
|---|---|---|
| EQ HC+ Behenamidopropyldimethylamine | 2:1 | 77 |
| EQ HC+ Behenamidopropyldimethylamine | 1:1 | 92 |
| Behenamidopropyldimethylamine | | 86 |
| EQ HC | | 111 |

The invention claimed is:

1. A solid cosmetic composition comprising:
   (a) from 13% to 25% dipalmitoylethyl hydroxyethylmonium methosulfate
   (b) from 7% to 15% behenamidopropyl dimethylamine and
   (c) from 65% to 70% cetearyl alcohol
   and wherein water content is 10 weight % or less and the composition is solid at room temperature.

2. The solid cosmetic composition according to claim 1, further comprising lactic acid.

3. The solid cosmetic composition according to claim 1, wherein the composition is free of organic and inorganic acids.

4. The solid cosmetic composition according to claim 1, wherein the water content of the composition is 0.2 weight % or less.

5. A method of preparing a hair conditioner composition, comprising a step of dispersing the solid cosmetic composition of claim 1 in water, wherein the method of preparation is carried out at a temperature within a range of 15° C. to 40° C. and wherein the water content of the hair conditioner composition is more than 95 weight %.

6. The method according to claim 5, further comprising a step of adding lactic acid to the hair conditioner composition.

7. A method of conditioning human hair, comprising applying the hair conditioner composition prepared according to claim 5 to hair.

8. The method of claim 5, wherein the solid cosmetic composition is dispersed in water at a temperature within a range of 18° C. to 35° C.

9. The method of claim 5, wherein the solid cosmetic composition is dispersed in water at a temperature within a range of 20° C. to 30° C.

10. The solid cosmetic composition of claim 1, wherein the water content is 5 weight % or less.

* * * * *